United States Patent [19]

van der Zel

[11] Patent Number: 4,992,297

[45] Date of Patent: Feb. 12, 1991

[54] CASTABLE PALLADIUM ALLOYS AND THEIR USE FOR MAKING DENTAL RESTORATIONS, ORNAMENTS, AND THE LIKE

[75] Inventor: Joseph M. van der Zel, Zwaag, Netherlands

[73] Assignee: Elephant Edelmetaal B.V., Hoorn, Netherlands

[21] Appl. No.: 346,333

[22] Filed: May 1, 1989

Related U.S. Application Data

[63] Continuation of Ser. No. 186,350, Apr. 26, 1988, abandoned.

[30] Foreign Application Priority Data

Apr. 28, 1987 [NL] Netherlands .......................... 8701001

[51] Int. Cl.$^5$ .......................... C23D 1/00; C22C 5/00; C22C 30/00
[52] U.S. Cl. ........................................ 427/2; 420/580; 420/463
[58] Field of Search ..................... 420/580, 463; 427/2

[56] References Cited

U.S. PATENT DOCUMENTS

| | | | |
|---|---|---|---|
| 4,063,937 | 12/1977 | Goltsou et al. | 420/463 |
| 4,350,526 | 9/1982 | Schaffer | 420/587 |
| 4,369,162 | 1/1983 | Wagner et al. | 420/502 |
| 4,399,096 | 8/1983 | Agarwal et al. | 420/463 |
| 4,451,639 | 5/1984 | Prasad | 420/463 |
| 4,526,750 | 7/1985 | Cascone | 420/463 |
| 4,539,176 | 9/1985 | Cascone | 420/463 |
| 4,539,177 | 9/1985 | Prasad | 420/463 |
| 4,576,789 | 3/1986 | Prasad | 420/463 |
| 4,608,229 | 8/1986 | Lanam et al. | 420/464 |
| 4,619,810 | 10/1986 | Prasad | 420/463 |
| 4,804,517 | 2/1989 | Schaffer et al. | 420/587 |

*Primary Examiner*—R. Dean
*Assistant Examiner*—David W. Schumaker
*Attorney, Agent, or Firm*—Stevens, Davis, Miller & Mosher

[57] ABSTRACT

This invention relates to novel alloys suitable for use in making dental restoration elements, such as crowns, inlays, and the like, and ornamental articles such as jewelry, ornaments and the like. The alloys are based on Pd, In and Ag and contain 25–50% by weight of Pd, 20–45% by weight of In and 20–50% by weight of Ag. The alloys may additionally contain minor proportions of certain other elements, they are castable, and have an esthetic yellow color.

1 Claim, No Drawings

CASTABLE PALLADIUM ALLOYS AND THEIR USE FOR MAKING DENTAL RESTORATIONS, ORNAMENTS, AND THE LIKE

This application is a continuation of application Ser. No. 186,350 filed Apr. 26, 1988, now abandoned.

This invention relates to castable palladium alloys with an esthetic yellow color, which alloys can be used in making jewelry, ornaments, and the like, and specifically are suitable for use in dentistry for the manufacture of crowns, inlays and other dental restorations in which porcelain or other coatings resembling porcelain are applied to imitate the color and form of natural teeth.

In dentistry, it is highly appreciated if an alloy on which porcelain is fired has a yellow color.

In addition, good bonding with porcelain and many other properties are desired, which ensure that no problems occur during production and service of the product.

Up until several years ago, gold alloys, generally gold-platinum alloys, have been used as yellow firing alloys. In connection with an increase in the gold price, researchers have looked for alternatives.

Such alternatives should at least have a low price, be easy to produce, possess an adequate thermal expansion, and bond well to dental porcelain formulations.

Thus U.S. Pat. No. 4,387,072 discloses dental casting alloys in which palladium is the major component, and the gold concentration has been reduced to no more than 5% by weight. The alloys contain 50-85% by weight of Pd, 5-40% by weight of Cu and/or Co, 1-15% by weight of Ga, 0-5% by weight of a metal from the group consisting of Ni, Au, In, Ru and Sn, 0-0.5% by weight of Re and/or Ir, and 0-1% by weight of boron. However, the prior alloys have a white color.

To save cost and at the same time have the possibility of using a yellow alloy, use has also been made of so-called aluminum bronze, a copper alloy with a high proportion of aluminum.

This alloy, which has a wide application, e.g. in ship's propellers, however, has proved to be noncorrosion-resistant in the buccal environment as a dental alloy.

The present invention provides castable palladium alloys having an attractive yellow color and to this effect comprise
25-50% by weight of palladium,
20-45% by weight of indium, and
20-50% by weight of silver.

Specifically, the invention relates to new castable palladium alloys with an esthetic yellow color and containing 35-50% by weight of Pd, 20-45% by weight of In, and 20-45% by weight of Ag, preferably 35-50% by weight of Pd, 25-45% by weight of In, and 20-40% by weight of Ag.

It has been found that, in connection with the desired yellow color, it is preferable for the palladium: indium atomic ratio in the alloys according to the invention to range from 1:2 to 2:1.

For that matter, it is known per se that combinations of palladium with indium can produce yellow colors, namely, according to FR-A-No. 2,543,488, when a layer of indium is applied galvanically to a substate of palladium. Through diffusion of the indium into the palladium, a $Pd_2In$ phase is formed in the metal, while more on the outside a layer of $\beta$-PdIn is formed. This latter has a yellow color. The intermetallic compound consisting of $\beta$-PdIn, however, is very brittle in character and is therefore unsuitable for use as a dental alloy.

Yet it has surprisingly proved possible to make an effectively castable alloy which meets all requirements of a dental firing alloy, is essentially free from gold, and nevertheless has an esthetic yellow color.

It will be clear that the alloy is in addition also suitable for casting so-called "full-metal" crowns, jewelry and ornaments, and for other uses where a high corrosion resistance and a yellow color are appreciated.

Although the alloys according to the invention preferably consist as to at least 70% by weight, more preferably as to at least 80% by weight, and most preferably as to at least 90% by weight of the elements Pd, In and Ag, the alloys may contain other elements, either in slight proportions as accidental impurities, or in deliberately chosen proportions as deliberate additives.

Although the alloys need not contain gold yet to possess the desired esthetic yellow color, gold may be added in proportions up to 10% by weight to increase their nobleness, which results in an increased corrosion resistance. Furthermore, gold increases hardness and hence brittleness.

Molybdenum, niobium, tungsten and chromium may be added in proportions of up to 10% by weight to decrease thermal expansion and increase strength.

Tantalum, titanium and rhenium also increase the strength of the alloy and in addition have a grain refining effect. Tantalum and titanium may also increase the high-temperature strength and hence dimensional stability during the firing of porcelain. The alloys may contain up to 6% by weight of Ta, Ti and/or Re.

The addition of up to 20% by weight of platinum, rhodium, ruthenium and/or iridium leads to a decrease in thermal expansion coefficient, an increase in corrosion resistance and gives the alloy a fine-grained structure.

An adverse effect of the addition, which to a lesser extent also applies to gold, is a deterioration of the yellow color.

To protect the alloy from oxidation during melting, and also to reduce the melting point of the alloy, it has been found that an addition of up to 5% by weight of zinc, tin, gallium, germanium, aluminum, silicon and/or boron may be advantageous.

For the firing of porcelain, it is necessary that the alloy exhibits an oxidation layer which is not too thick, because this may adversely affect bonding strength. It has been found that addition of up to 3% by weight of scandium, yttrium, lanthanum and other rare earths reduce the oxidation of the alloys, which results in improved bonding with porcelain.

The alloys of this invention can be fired with all modern color-stable porcelains with a high coefficient of thermal expansion, provided after firing at 980° C the porcelain is maintained at 800° C for some time, for example, for 10 minutes, before being allowed to cool to room temperature. In that case, no cracks occur in the porcelain during firing, and the alloys exhibit a good bonding strength with the porcelain.

The invention is illustrated in and by the following examples.

EXAMPLES

Alloys with the specified compositions are weighed and molten under argon (400 Torr) in a zirconia crucible in a vacuum induction furnace.

The palladium was 99.96%, the silver 99.9% and the indium 99.999% pure.

The alloys were cast into a steel mold. Thereafter a test bar was cast from the alloys by a method conventionally used in dental engineering. In an electrically heated muffle furnace, the alloys were molten in a graphite crucible at 1400° C, and then centrifugally cast into a mold consisting of phosphate-bonded molding sand preheated at 900° C.

In the following table, the compositions of the alloys tested and the respective properties are specified. Tensile strength, yield point, elongation at break and hardness were measured with test pieces after a heat treatment at 950° C for 10 minutes, followed by a heat treatment at 600° C for 15 minutes. Examples 1, 4, 6 and 9 do not concern alloys of this invention and merely serve for comparison to show the importance of the requirement that the alloys contain 35–50% by weight of Pd, 25–45% by weight of In and 25–50% by weight of Ag.

to have broken during casting. The poor resistance which the alloy exhibits against shrinkage stresses occurring during cooling in the molding mass makes the alloy unsuitable for use. Moreover the alloy had a poor strength and exhibited a brittle behavior by breaking when subjected to minor loads without permanent deformation. The alloy exhibited a reddish-yellow color.

By adding more silver to the alloy, the alloy became less brittle and at higher silver concentrations, this brittle behavior did not manifest itself at all. At the same time, at 25% by weight of silver (Example 2), the alloy gets a richly-yellow color.

An adverse effect of silver is the increase in coefficient of thermal expansion. For firing porcelain on metal, the coefficient of thermal expansion of the porcelain and the metal should preferably be as close together as possible. When the silver content is too high, the expansion of the alloy becomes too different from that of the porcelain. Problems can be avoided, however, by inserting a slow cooling phase after the firing of the por-

TABLE

| Metal | Example No. | | | | | | | | |
|---|---|---|---|---|---|---|---|---|---|
| | 1 (comp.) | 2 | 3 | 4 (comp.) | 5 | 6 (comp.) | 7 | 8 | 9 (comp.) |
| Pt | — | — | 5 | 1 | 2 | — | — | — | 1 |
| Pd | 51 | 40 | 37 | 45 | 36 | 25 | 38 | 39 | 37 |
| Ag | 7 | 25 | 28 | 13 | 28 | — | 27 | 28 | — |
| In | 42 | 32 | 29 | 35 | 29 | 22 | 32 | 30 | 31 |
| Au | — | — | — | — | 0.5 | 53 | — | — | 30 |
| Ir | — | — | 0.2 | 0.2 | — | — | 0.2 | 0.2 | — |
| Ru | — | — | — | 0.1 | 0.3 | — | — | — | — |
| Mo | — | — | — | 3 | — | — | — | — | — |
| Nb | — | — | — | — | — | — | 2.7 | — | — |
| Zn | — | 3 | — | — | — | — | — | — | — |
| Ce | — | — | — | — | — | — | 0.1 | — | 0.1 |
| Ta | — | — | — | — | — | — | — | 1.8 | — |
| Sn | — | — | 0.8 | — | — | — | — | 1.0 | — |
| Colour | reddish yellow | yellow | light yellow | light yellow | light yellow | light yellow | yellow | yellow | light yellow |
| Vickers Hardness HV | brittle | 258 | 200 | brittle | 234 | 300 | 190 | 210 | brittle |
| tensile strength, kg/mm$^2$ | — | 46.4 | 54.6 | — | 44.7 | 24.2 | 22.3 | 41.0 | — |
| Yield point, kg/mm$^2$ | — | 41.0 | 44.7 | — | 40.0 | 24.2 | 22.3 | 33.0 | — |
| Elongation at break, % | — | 0.5 | 1.5 | — | 0.3 | 0.0 | 0.0 | 2.1 | — |
| Linear expansion coefficient 10$^{-6}$/°C | 16.2 | 17.1 | 16.7 | 16.2 | 16.7 | 16.0 | 17.3 | 16.9 | 16.4 |

Of the alloys tested, the alloy of Example 8 turned out to have the best combination of properties.

From this alloy according to the invention, which contained 39% Pd, 28% Ag, 30% In, 0.2% Ir, 1.8% Ta and 1% Sn, tents of crowns and a few bridges were cast, and a color-stable porcelain was fired against these at 950° C. No cracks were found in the porcelain in any of the restorations. When the porcelain was removed by hammering, a large amount of porcelain remained bonded to the metal, which means that the bond strength with the metal is higher than the strength of the porcelain proper.

Moreover, the alloy was polished and then allowed to lie in 1N Na$_2$S-0.2 N NaCl solution for 7 days.

After 7 days, the alloy was examined under the microscope at magnification 200. No effects of heat tinting were observed. In most cases, this test is a good indication for the corrosion behavior in the mouth.

The comparative alloy of Example 1 was found after being removed from the molding sand (from the mold)

celain during cooling to room temperature, which results in a higher contraction of the porcelain, so that it comes to be closer to the higher contraction of the alloy. It is sufficient if the slow cooling process extends down to a temperature of about 800° C. No particular requirements are imposed upon the further cooling from about 800° C to room temperature.

I claim:

1. A process for making crack-free dental restorations comprising coating with porcelain a castable palladium alloy in the form of a dental restoration containing 35–50 wt % Pd, 20–45 wt % In, 20–45 wt % Ag, up to 6 wt % tantalum, titanium and/or rhenium, up to 5 wt % zinc, tin, gallium, germanium, aluminum, silicon and/or boron and an amount up to 3 wt % scandium, lanthanum, yttrium and/or rare earths to effect reduction of the thickness of an oxide layer on said alloy and thereby improve bonding with porcelain and firing said coated alloy to form a crack-free dental restoration.

* * * * *